US007222520B2

United States Patent
Hobert

(10) Patent No.: US 7,222,520 B2
(45) Date of Patent: May 29, 2007

(54) FITNESS FOR USE OF FIBERGLASS INSULATION

(75) Inventor: Ward Thomas Hobert, Golden, CO (US)

(73) Assignee: Johns Manville, Denver, CO (US)

( * ) Notice: Subject to any disclaimer, the term of this patent is extended or adjusted under 35 U.S.C. 154(b) by 93 days.

(21) Appl. No.: 10/887,023

(22) Filed: Jul. 8, 2004

(65) Prior Publication Data

US 2006/0005612 A1    Jan. 12, 2006

(51) Int. Cl.
*G01N 5/02* (2006.01)

(52) U.S. Cl. ......................................................... 73/73

(58) Field of Classification Search ............... 73/73–77
See application file for complete search history.

(56) References Cited

U.S. PATENT DOCUMENTS

| 4,194,559 | A | * | 3/1980 | Eastman | 165/104.26 |
| 4,539,377 | A | * | 9/1985 | Hefner, Jr. | 525/401 |
| 4,695,060 | A | * | 9/1987 | Pilgrim | 273/404 |
| 4,838,705 | A | * | 6/1989 | Byers et al. | 374/14 |
| 5,215,407 | A | * | 6/1993 | Brelsford | 405/63 |
| 5,649,708 | A | * | 7/1997 | Podlesny | 273/403 |
| 2002/0110739 | A1 | * | 8/2002 | McEwen et al. | 429/324 |

OTHER PUBLICATIONS

Reference "A", "Outdoor Forums: uptate on my projects", Internet publication, comment posted by HNSB on Dec. 30, 2003.*
Reference "B", Internet publication, Comment posted by HNSB on Jan. 9, 2004.*

* cited by examiner

*Primary Examiner*—Robert Raevis
(74) *Attorney, Agent, or Firm*—Robert D. Touslee; Timothy G. Hofmeyer

(57) ABSTRACT

A method for determining the water resistance of glass fiber based insulation to wetting by water is disclosed. The method generally comprise the steps of placing a sample of insulation into contact with a source of water for a defined period of time; removing the insulation sample from the water containing surface; draining the sample for a prescribed period of time, and determining the water resistance according to certain formulas or observations.

3 Claims, No Drawings

FITNESS FOR USE OF FIBERGLASS INSULATION

TECHNICAL FIELD

The invention relates to a method for evaluating the water resistance of binder-coated fiberglass products. Both qualitative and quantitative methods are provided.

BACKGROUND OF THE INVENTION

Fibrous glass insulation ("fiberglass" or "glass fiber" insulation) products generally comprise matted glass fibers bonded together by a binder that is often a cured thermoset polymeric material. Molten streams of glass are drawn into fibers of random lengths and blown into a forming chamber where they are randomly deposited as a mat onto a traveling conveyor. The fibers, while in transit in the forming chamber, and while still hot from the drawing operation, are sprayed with the binder(often aqueous-based). The coated fibrous mat is transferred to a curing oven where heated air, for example, is blown through the mat to cure the binder and rigidly bond the glass fibers together.

Fiberglass binders have a variety of uses ranging from stiffening applications where the binder is applied to woven or non-woven fiberglass sheet goods and cured, producing a stiffer product; thermo-forming applications wherein the binder resin is applied to sheet or lofty fibrous product following which it is dried and optionally B-staged to form an intermediate but yet curable product; and to fully cured systems such as building insulation.

Fiberglass binders used in the present sense should not be confused with matrix resins which are an entirely different and non-analogous field of art. While sometimes termed "binders", matrix resins act to fill the entire interstitial space between fibers, resulting in a dense, fiber reinforced product where the matrix must translate the fiber strength properties to the composite, whereas "binder resins" as used herein are not space-filling, but rather coat only the fibers, and particularly the junctions of fibers. Fiberglass binders also cannot be equated with paper or wood product "binders" where the adhesive properties are tailored to the chemical nature of the cellulosic substrates. Many such resins, e.g. urea/formaldehyde and resorcinol/formaldehyde resins, are not suitable for use as fiberglass binders. One skilled in the art of fiberglass binders would not look to cellulosic binders to solve any of the known problems associated with fiberglass binders.

Binders useful in fiberglass insulation products generally require a low viscosity in the uncured state, yet characteristics so as to form a rigid thermoset polymeric mat for the glass fibers when cured. A low binder viscosity in the uncured state is required to allow the mat to be sized correctly. Also, viscous binders tend to be tacky or sticky and hence they lead to accumulation of fiber on the forming chamber walls. This accumulated fiber may later fall onto the mat causing dense areas and product problems. A binder which forms a rigid matrix when cured is required so that a finished fiberglass thermal insulation product, when compressed for packaging and shipping, will recover to its specified vertical dimension when installed in a building.

From among the many thermosetting polymers, numerous candidates for suitable thermosetting fiber-glass binder resins exist. However, binder-coated fiberglass products are often of the commodity type, and thus cost becomes a driving factor, generally ruling out such resins as thermosetting polyurethanes, epoxies, and others. Due to their excellent cost/performance ratio, the resins of choice in the past have been phenol/formaldehyde resins. Phenol/formaldehyde resins can be economically produced, and can be extended with urea prior to use as a binder in many applications. Such urea-extended phenol/formaldehyde binders have been the mainstay of the fiberglass insulation industry for years.

Over the past several decades, however, minimization of volatile organic compound emissions (VOCs) both on the part of the industry desiring to provide a cleaner environment, as well as by Federal regulation, has led to extensive investigations into not only reducing emissions from the current formaldehyde-based binders, but also into candidate replacement binders. For example, subtle changes in the ratios of phenol to formaldehyde in the preparation of the basic phenol/formaldehyde resole resins, changes in catalysts, and addition of different and multiple formaldehyde scavengers, has resulted in considerable improvement in emissions from phenol/formaldehyde binders as compared with the binders previously used. However, with increasing stringent Federal regulations, more and more attention has been paid to alternative binder systems which are free from formaldehyde.

One particularly useful formaldehyde-free binder system employs a binder comprising a polycarboxy polymer and a polyol. Formaldehyde-free resins are those which are not made with formaldehyde or formaldehyde-generating compounds. Formaldehyde-free resins do not emit appreciable levels of formaldehyde during the insulation manufacturing process and do not emit formaldehyde under normal service conditions. Use of this binder system in conjunction with a catalyst, such as an alkaline metal salt of a phosphorous-containing organic acid, results in glass fiber products that exhibit excellent recovery and rigidity properties.

Fiberglass products, such as fiberglass insulation, are exposed to a variety of environmental conditions that can adversely affect the performance of the product. One factor or condition that can detrimentally affect the performance of fiberglass insulation is exposure to water both during storage and in use. Absorption of water can adversely affect the properties of the fiberglass product and can cause degradation of the product.

It is useful, therefore, to be able to evaluate the ability of a fiberglass product to resist water, more specifically, to resist absorption of water.

BRIEF SUMMARY OF THE INVENTION

The present invention is directed to a system and method for evaluating the water resisting properties of glass fiber products, specifically insulation. Both qualitative and quantitative procedures are provided.

The method provides for determining the water resistance of glass fiber based insulation to water by placing a sample of insulation into contact with a water for a specific period of time. One method for qualitatively determining water resistance is to observe whether the sample remains on the surface of the water, or whether any portion of the sample sinks below the surface.

A more quantitative method involves determining the amount of water absorbed by the sample. The method comprises placing a sample of fiberglass on a liquid surface that contains water or a solid surface flooded or covered with a water containing solution. The method can be used to generate a qualitative or quantitative measure of water resistance. The disclosed invention is useful with any fiberglass product that is initially buoyant to water, especially fiberglass insulation.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description.

DETAILED DESCRIPTION OF THE INVENTION

Both formaldehyde-based and formaldehyde-free binder composition can be adversely affected by exposure to water. Wet insulation is very difficult to handle and install. In addition, absorption of water by fiberglass insulation can adversely affect its insulation ability. Finally, prolonged exposure to water can result in degradation of the physical and chemical properties of the product. It is therefore useful to be able to determine the water resistance/repellency of fiberglass products, especially fiberglass insulation.

It has been unexpectedly found that insulation can be repeatably, and accurately, tested to predict the effects of water exposure, infiltration, or absorption/adsorption, heretofore referred to as "water resistance" using tests in which at least a portion of an insulation sample is brought into contact with a surface containing at least a portion of liquid water for a period of time. Insulation that has directly contacted a source of liquid water often cannot be used because it is difficult to handle and may have suffered degradation in properties. Property degradation is meant to include but not limited to mechanical properties, transport properties, chemical properties and the like.

The method of the invention is determining the water resistance of both fiberglass products manufactured with either formaldehyde-containing or formaldehyde-free binder compositions. As used herein, the term "formaldehyde-free" means that the resin or binder composition is substantially free of formaldehyde and/or does not liberate formaldehyde as a result of drying or curing.

The method generally involves preparing a specimen of fiberglass product for testing, placing the specimen in contact with water and determining the water resistance of the specimen. The water resistance can be determined by either qualitative or quantitative techniques.

The method of the invention can be used to evaluate the water resistance of fiberglass products where its ability to resist water affects the products performance. As described above, water resistance is particularly important for fiberglass insulation; however, there are other applications of fiberglass where water resistance can be important.

The product samples should be chosen so as to provide an adequate representation of the properties of the material being tested. For fiberglass insulation, it is preferable to use at least three samples from the same lot or batch to obtain results that are representative of the entire lot or batch. However, fewer or more samples can be used without deviating from the spirit of the method.

In the case of fiberglass insulation, the sample may be an existing batt or roll and may be taken from the production line at any point after curing from each sample, specimens are prepared for testing. This is usually done by cutting a sample from the batt or roll. The size of the specimen should be sufficient to obtain a representative evaluation of the product and may vary depending on such variables as the label thickness of the product. For example, for fiberglass insulation having a label thickness $\geq 3.5"$ (8.9 cm), the preferred specimen size is 6"×6" (15.25 cm×15.25 cm). For fiberglass insulation with a label thickness of <3.5" (8.9 cm), a 6"×2" (15.25 cm×5.1 cm) specimen is preferred.

The specimen is then placed in contact with water. The water can be in the form of either a water bath or merely a layer of water on a clean horizontal surface. While water from any source can be used, the water should be free of contaminants, especially those that reduce surface tension (e.g. soaps, detergents, surfactants, alcohols). While the water bath can be used for any number of tests, it is preferable to change the bath when there is a suspect result or a significant increase in failures.

Where a water bath is used, the bath should be sufficiently large to accommodate the specimen without the specimen touching the sides of the bath. The depth of the bath should be sufficient to provide enough water for a meaningful result. For evaluation of fiberglass insulation, a bath depth of $\geq 3"$ (7.68 cm) is preferred; however, lower or greater depths can be employed without deviating from the spirit and scope of the invention.

Where the specimen is exposed to a pool of water on a flat surface, sufficient water should be provided to yield a meaningful result. In the case of a qualitative test, the amount should be sufficient to provide an observable result. For the quantitative test, the amount should be sufficient to provide a significant change in weight of the sample.

The specimen is then brought in contact with the water. In the case of fiberglass insulation, this is preferably done by gently laying the specimen along one of the cut sides on the surface of the water. Placing the specimen in the bath on the cut side increases the propensity of the sample to absorb water. Generally, the glass fibers are oriented parallel to the product surfaces. Absorption is aided by capillary action (wicking) along the cut edges. The sample is then left in contact with the water for a period sufficient to allow the product to absorb water or for water to migrate into the sample. Three hundred seconds ±15 seconds is preferred for fiberglass insulation; however, longer or shorter periods can be used. While the sample is in contact with the water, care should be taken not to disturb the sample.

Determination of the water resistance of the sample after exposure to water can be done by either qualitative or quantitative means. While there are numerous means for determining water resistance, the following methods are useful for determining the water resistance of fiberglass insulation.

When a water bath is used, one qualitative method that can be used is to observe whether the sample remains on the surface of the water of the prescribed period or whether any part of the sample has submerged below the surface. In its simplest form, the sample is deemed to have passed if it remains on the surface. If any part submerges, the product fails.

One variation of this method is to measure the depth to which the product has submerged. In this method, the distance from the surface of the bath to the lowest part of the sample below the surface is measured. The measurement can be made using a ruler or similar device. The depth to which the product submerges is an indication of its water resistance. The further the product sinks or submerges, the worse its resistance. Where multiple samples are tested, the measurements should be averaged and the evaluation should be based on the average distance.

Where the sample is exposed to water on a flat surface, a qualitative method that can be used is to visually inspect the sample after the prescribed period has elapsed to see if any water has been absorbed by or migrated into the sample. A dye may be added to the water before the test begins to aid their visual inspection. A simple pass/fail evaluation can be made based on whether or not the sample contains any visually appreciable amounts of water.

A quantitative method for evaluating the water resistance of the product can be done by determining the amount of water retained by the sample after it is exposed to water. In this method, the weight of each sample is determined prior to exposure to water. The samples are then exposed to water for a specified period of time. The sample is then moved from the water in a manner that prevents additional wetting or absorption. At least a portion of the absorbed water is allowed to drain from the sample. This is typically accomplished by suspending the sample over the bath or wetted surface for a period of about 30 seconds. The weight of the wetted sample is then determined and compared with the weight of the sample at the start of the test. Where multiple samples are used, the results may be averaged. Alternatively, the sample can be removed from the bath and immediately placed in a pan. The sample, the pan and any water collected in the pan are then weighed. The weight of the empty pan is then subtracted from the measured weight to give the wet weight of the specimen.

The results may be reported simply as the weight gained in the units measured (e.g. grams, ounces) or as a percent of the initial weight, which is calculated as:

$$RW = 100 \times (WW-DW)/DW$$

where RW is retained weight, WW is wet weight of the specimen and DW is the dry or initial weight of the specimen. The measured or calculated values can then be compared with an established norm to determine if the product exhibits the desired water resistance.

EXAMPLES

The following is offered as an example of the invention and should not be construed as limiting the invention.

Four samples of commercial R19 insulations were obtained. Three 6"×6" (15.25 cm×15.25 cm) specimens of each sample were prepared and weighed. The samples were then floated in a water bath with a depth of from about 3 (7.62 cm) to about 3.5 (8.9 cm) inches for about 300 seconds. The samples were then removed from the water bath and allowed to drain for about 30 seconds. Each sample was then weighed and percent retained water was calculated as described above. The results were sample A: 820% retained water; sample B: 96% retained water; sample C: 47% retained water, and sample D: 22% retained water. A retained water percentage of less than about 50% is considered acceptable.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method for determining the water resistance of a fiberglass insulation comprising:
   preparing a sample of fiberglass insulation;
   placing the sample on the surface of water;
   determining the amount of water absorbed by the sample by determining the extent to which the sample sinks below the surface of the water.

2. The method of claim 1 where the sample is placed on the surface of the water for at least about 300 seconds before determining if any portion of the sample has sunk below the surface.

3. The method of claim 1 further comprising the step of measuring the depth to which the sample has sunk below the surface of the water.

* * * * *